(12) United States Patent
Bostic et al.

(10) Patent No.: US 12,027,243 B2
(45) Date of Patent: Jul. 2, 2024

(54) SYSTEM AND METHOD FOR DETERMINING HEALTHCARE RELATIONSHIPS

(71) Applicant: HC1 INSIGHT LLC, Indianapolis, IN (US)

(72) Inventors: Brad Bostic, Carmel, IN (US); Travis Morgan, Indianapolis, IN (US); Mark Preston, Indianapolis, IN (US); William E Robinson, Speedway, IN (US); David Sutton, Indianapolis, IN (US); Jason Wolfgang, Indianapolis, IN (US); Alicia Bernasconi, Indianapolis, IN (US); Laura Breedlove, Indianapolis, IN (US); Charles J Clarke, Indianapolis, IN (US); Christina Deximo, Indianapolis, IN (US); Helen Malick, Coppell, TX (US)

(73) Assignee: HC1 INSIGHTS, INC., Indianapolis, IN (US)

(*) Notice: Subject to any disclaimer, the term of this patent is extended or adjusted under 35 U.S.C. 154(b) by 279 days.

(21) Appl. No.: 15/898,660

(22) Filed: Feb. 18, 2018

(65) Prior Publication Data

US 2018/0240536 A1    Aug. 23, 2018

Related U.S. Application Data

(60) Provisional application No. 62/460,310, filed on Feb. 17, 2017.

(51) Int. Cl.
*G16H 10/60* (2018.01)
*G06F 16/951* (2019.01)
(Continued)

(52) U.S. Cl.
CPC ........... *G16H 10/60* (2018.01); *G06F 16/951* (2019.01); *G16H 50/20* (2018.01); *G16H 50/70* (2018.01)

(58) Field of Classification Search
CPC ........ G16H 10/60; G16H 50/70; G16H 50/20; G06F 16/951
(Continued)

(56) References Cited

U.S. PATENT DOCUMENTS

| | | |
|---|---|---|
| 10,558,925 B1 | 2/2020 | Flor et al. |
| 2002/0042726 A1 | 4/2002 | Mayaud |

(Continued)

FOREIGN PATENT DOCUMENTS

| | | |
|---|---|---|
| WO | 2013122979 A1 | 8/2013 |
| WO | 2015148614 A1 | 10/2015 |

OTHER PUBLICATIONS

PCT International Search Report and Written Opinion dated Jul. 2, 2015 for International Application No. PCT/US2015/022408, 9 pages.

(Continued)

*Primary Examiner* — Michael Tomaszewski
(74) *Attorney, Agent, or Firm* — RMCK Law Group, PLC

(57) ABSTRACT

Technologies for determining healthcare relationships include a healthcare insight computing device communicatively coupled to multiple patient data providers. The healthcare insight computing device is configured to determine one or more relationships between received data and previously received patient data associated with one or more patients. The healthcare insight computing device is further configured to correlate the ingested data as a function of the determined relationships and enrich the correlated patient data to form a new data element. Additionally, the healthcare (Continued)

insight computing device is configured to transmit the new data element to a raw data cluster such that visual representations of the data elements of the raw data cluster and the relationships there between can be displayed. Additional embodiments are described herein.

17 Claims, 4 Drawing Sheets

(51) Int. Cl.
*G16H 50/20* (2018.01)
*G16H 50/70* (2018.01)

(58) Field of Classification Search
USPC .......................................................... 705/2–3
See application file for complete search history.

(56) References Cited

U.S. PATENT DOCUMENTS

| | | | |
|---|---|---|---|
| 2003/0167189 A1 | 9/2003 | Lutgen et al. | |
| 2004/0019502 A1 | 1/2004 | Leaman et al. | |
| 2004/0122702 A1* | 6/2004 | Sabol ..................... | G06Q 10/10 706/45 |
| 2004/0122706 A1* | 6/2004 | Walker .................. | G16H 50/20 706/45 |
| 2005/0048666 A1 | 3/2005 | Larson et al. | |
| 2005/0102159 A1 | 5/2005 | Mondshine | |
| 2005/0108052 A1 | 5/2005 | Omaboe | |
| 2005/0165623 A1 | 7/2005 | Landi et al. | |
| 2007/0112586 A1* | 5/2007 | Dettinger ............... | G16H 10/60 705/2 |
| 2008/0015894 A1 | 1/2008 | Miller et al. | |
| 2008/0022370 A1 | 1/2008 | Beedubail et al. | |
| 2008/0046292 A1 | 2/2008 | Myers et al. | |
| 2008/0140484 A1 | 6/2008 | Akerman | |
| 2008/0228522 A1 | 9/2008 | Davis et al. | |
| 2008/0280772 A1 | 11/2008 | Wong et al. | |
| 2010/0076786 A1 | 3/2010 | Dalton et al. | |
| 2010/0241448 A1 | 9/2010 | Firminger et al. | |
| 2011/0082712 A1 | 4/2011 | Eberhardt, III et al. | |
| 2011/0255782 A1 | 10/2011 | Welling et al. | |
| 2011/0288886 A1 | 11/2011 | Whiddon et al. | |
| 2011/0295621 A1 | 12/2011 | Farooq et al. | |
| 2012/0022897 A1 | 1/2012 | Shafer | |
| 2012/0191466 A1 | 7/2012 | Quint et al. | |
| 2012/0203798 A1 | 8/2012 | Gifford et al. | |
| 2012/0239430 A1 | 9/2012 | Corfield | |
| 2012/0253139 A1 | 10/2012 | Maman et al. | |
| 2012/0283546 A1 | 11/2012 | Zuehlsdorff et al. | |
| 2012/0284052 A1 | 11/2012 | Saukas et al. | |
| 2012/0303388 A1 | 11/2012 | Vishnubhatla et al. | |
| 2013/0006668 A1 | 1/2013 | Arkel et al. | |
| 2013/0080379 A1 | 3/2013 | Stergiou et al. | |
| 2013/0179450 A1 | 7/2013 | Chitiveli | |
| 2013/0197936 A1 | 8/2013 | Willich | |
| 2013/0218592 A1 | 8/2013 | Hashmat | |
| 2013/0310726 A1 | 11/2013 | Miller et al. | |
| 2013/0346104 A1 | 12/2013 | Pillai | |
| 2014/0002234 A1 | 1/2014 | Alwan | |
| 2014/0012790 A1 | 1/2014 | Oberkampf et al. | |
| 2014/0052460 A1 | 2/2014 | Grossman et al. | |
| 2014/0067408 A1 | 3/2014 | Aach | |
| 2014/0108024 A1 | 4/2014 | Evans et al. | |
| 2014/0114676 A1 | 4/2014 | Holmes | |
| 2014/0149128 A1 | 5/2014 | Getchius | |
| 2014/0149139 A1 | 5/2014 | Bowen, Jr. et al. | |
| 2014/0167917 A2 | 6/2014 | Wallace et al. | |
| 2014/0236617 A1 | 8/2014 | Oberfest et al. | |
| 2014/0246334 A1 | 9/2014 | Bosch et al. | |
| 2014/0279807 A1 | 9/2014 | Dimitrijevic | |
| 2014/0324825 A1 | 10/2014 | Gopinath et al. | |
| 2014/0357961 A1 | 12/2014 | Meltzer et al. | |
| 2015/0039344 A1 | 2/2015 | Kinney et al. | |
| 2015/0058028 A1 | 2/2015 | Su et al. | |
| 2015/0058039 A1 | 2/2015 | Shiloh | |
| 2015/0066910 A1 | 3/2015 | Bleach | |
| 2015/0088540 A1 | 3/2015 | Lo et al. | |
| 2015/0100349 A1 | 4/2015 | Lacy et al. | |
| 2015/0193583 A1* | 7/2015 | McNair .................. | G16H 50/20 705/2 |
| 2015/0213206 A1 | 7/2015 | Amarasingham et al. | |
| 2015/0213223 A1 | 7/2015 | Amarasingham et al. | |
| 2015/0286792 A1 | 10/2015 | Gardner et al. | |
| 2015/0324527 A1 | 11/2015 | Siegel et al. | |
| 2015/0379201 A1* | 12/2015 | Varadarajan ............ | G16Z 99/00 705/3 |
| 2016/0004820 A1 | 1/2016 | Moore | |
| 2016/0019349 A1 | 1/2016 | Ross et al. | |
| 2016/0092641 A1 | 3/2016 | Delaney et al. | |
| 2016/0117468 A1 | 4/2016 | Mankad et al. | |
| 2016/0125170 A1 | 5/2016 | Abramowitz | |
| 2016/0147945 A1 | 5/2016 | MacCarthy et al. | |
| 2016/0188822 A1 | 6/2016 | Ryan et al. | |
| 2016/0243359 A1 | 8/2016 | Sharma | |
| 2016/0350919 A1 | 12/2016 | Steigauf et al. | |
| 2016/0357910 A1 | 12/2016 | Ghouri et al. | |
| 2017/0061152 A1 | 3/2017 | Bostic et al. | |
| 2017/0083681 A1 | 3/2017 | Sprintz et al. | |
| 2017/0116389 A1 | 4/2017 | Matlin et al. | |
| 2017/0169173 A1 | 6/2017 | Snow, Jr. et al. | |
| 2017/0169175 A1 | 6/2017 | Graff et al. | |
| 2017/0277838 A1 | 9/2017 | Derer | |
| 2017/0286621 A1 | 10/2017 | Cox et al. | |
| 2017/0300648 A1 | 10/2017 | Charlap | |
| 2017/0308652 A1 | 10/2017 | Ligon | |
| 2018/0001184 A1 | 1/2018 | Tran et al. | |
| 2018/0020186 A1 | 1/2018 | Gurmu | |
| 2018/0039731 A1 | 2/2018 | Szeto | |
| 2018/0114595 A1 | 4/2018 | Stern | |
| 2018/0121606 A1 | 5/2018 | Allen et al. | |
| 2018/0137244 A1 | 5/2018 | Sorenson et al. | |
| 2018/0166172 A1 | 6/2018 | Fidone et al. | |
| 2018/0174673 A1 | 6/2018 | Defrank et al. | |
| 2018/0197625 A1 | 7/2018 | Lobach | |
| 2018/0253840 A1 | 9/2018 | Tran | |
| 2018/0261325 A1 | 9/2018 | Nanos | |
| 2018/0330060 A1 | 11/2018 | Biles et al. | |
| 2018/0330824 A1 | 11/2018 | Athey et al. | |
| 2018/0333063 A1 | 11/2018 | Muchhala et al. | |
| 2018/0342324 A1 | 11/2018 | Cha et al. | |
| 2018/0374580 A1 | 12/2018 | Gupta et al. | |
| 2019/0005187 A1 | 1/2019 | Costello et al. | |
| 2019/0005195 A1 | 1/2019 | Peterson et al. | |
| 2019/0026438 A1 | 1/2019 | Ma et al. | |
| 2019/0108912 A1 | 4/2019 | Spurlock, III et al. | |
| 2019/0138692 A1 | 5/2019 | Guo et al. | |
| 2019/0188410 A1 | 6/2019 | Briscoe et al. | |
| 2019/0198144 A1 | 6/2019 | Blackley et al. | |
| 2019/0198169 A1 | 6/2019 | Satyanarayana et al. | |
| 2019/0214145 A1 | 7/2019 | Kurek et al. | |
| 2019/0287679 A1 | 9/2019 | Beck et al. | |
| 2019/0304604 A1 | 10/2019 | Kupersmith et al. | |
| 2019/0355451 A1 | 11/2019 | Clark | |
| 2019/0355479 A1 | 11/2019 | Carlson et al. | |
| 2019/0355481 A1 | 11/2019 | Lamb et al. | |
| 2019/0385738 A1 | 12/2019 | Hoelzer et al. | |
| 2020/0004746 A1 | 1/2020 | Randall et al. | |
| 2020/0335224 A1 | 10/2020 | Sreenivasan et al. | |

OTHER PUBLICATIONS

U.S. Appl. No. 15/120,208, filed Aug. 19, 2016, Bostic et al.
Centers for Disease Control and Prevention, "Calculating Total Daily Dose of Opiods for Safer Dosage," https://web.archive.org/web/20171209014431/https://www.cdc.gov/drugoverdose/pdf/calculating_total_daily_dose-a.pdf, Dec. 2017, 2 pages.
U.S. Appl. No. 17/204,611, filed Mar. 17, 2021, Bostic et al..
U.S. Appl. No. 17/205,005, filed Mar. 18, 2021, Bostic et al..
U.S. Appl. No. 17/205,049, filed Mar. 18, 2021, Bostic et al..
U.S. Appl. No. 17/205,068, filed Mar. 18, 2021, Bostic et al..
U.S. Appl. No. 17/203,984, filed Mar. 17, 2021, Bostic et al..

(56) References Cited

OTHER PUBLICATIONS

U.S. Appl. No. 17/204,019, filed Mar. 17, 2021, Bostic et al..
U.S. Appl. No. 17/204,040, filed Mar. 17, 2021, Bostic et al..
U.S. Appl. No. 17/204,070, filed Mar. 17, 2021, Bostic et al..
U.S. Appl. No. 17/204,081, filed Mar. 17, 2021, Bostic et al..
U.S. Appl. No. 17/204,104, filed Mar. 17, 2021, Bostic et al..
U.S. Appl. No. 17/204,131, filed Mar. 17, 2021, Bostic et al.
U.S. Appl. No. 17/205,013, filed Mar. 18, 2021, Bostic et al..
U.S. Appl. No. 17/205,033, filed Mar. 18, 2021, Bostic et al..
U.S. Appl. No. 17/205,105, filed Mar. 18, 2021, Bostic et al.
U.S. Appl. No. 17/205,126, filed Mar. 18, 2021, Bostic et al..
U.S. Appl. No. 16/778,377, filed Jan. 31, 2020, Bostic et al..
U.S. Appl. No. 16/825,396, filed Mar. 20, 2020, Bostic et al..
U.S. Appl. No. 17/023,516, filed Sep. 17, 2020, Bostic et al..
U.S. Appl. No. 17/204,557, filed Mar. 17, 2021, Bostic et al..
U.S. Appl. No. 16/535,863, filed Aug. 8, 2019, Bostic et al..

* cited by examiner

SYSTEM AND METHOD FOR DETERMINING HEALTHCARE RELATIONSHIPS

PRIORITY

This application claims priority to U.S. Provisional Patent Application No. 62/460,310, filed Feb. 17, 2017, which is incorporated in its entirety, by reference, herein.

TECHNICAL FIELD OF THE DISCLOSED EMBODIMENTS

The presently disclosed embodiments generally relate to the analysis of patient data, and more particularly, to a system and method for determining healthcare relationships.

BACKGROUND OF THE DISCLOSED EMBODIMENTS

Many nations spend an equivalent of over ten percent of a country's Gross Domestic Product (GDP) on healthcare each year. For example, in 2010, healthcare expenditures in the United States were equivalent to 17.9% of GDP. The Organization for Economic Co-operation and Development (OECD) estimates that developed countries spend, on average, 9.5% of GDP on healthcare.

Many patients with undiagnosed chronic conditions consume expensive services that treat ailments associated with their chronic condition without treating the underlying chronic condition itself. It has been estimated that these patients' overall medical costs can be up to six times higher pre-diagnosis than post-diagnosis. In other words, diagnosis of a chronic condition can lessen a patient's healthcare costs dramatically.

Today, health practitioners are generally not equipped to identify many of these chronic conditions at time of visit. If an undiagnosed chronic condition patient enters the emergency room seeking care for a specific symptom, a doctor may treat that specific symptom and release the patient without understanding how that specific symptom may be a sign of the chronic condition. That same patient might enter an emergency room with various symptoms over the course of months or even years without any individual doctor identifying that each symptom was associated with the same chronic condition that, if treated earlier on, could have removed the bulk of these emergency room visits.

For example, a patient may enter the emergency room one week for a bladder infection, a different emergency room the next week for headaches, and a third emergency room the third week with dry mouth. When each symptom is diagnosed individually, the diagnoses may be appropriate; however, that patient may have an underlying condition (e.g., diabetes) that may not be diagnosed because the symptoms were not analyzed on the whole. Accordingly, if the doctors from each of the different emergency rooms are not communicating with each other to diagnose the symptoms on the whole, the underlying condition may only be diagnosed after great expenditure by the patient chasing each symptom independently.

Additionally, there can also be warning signs for many chronic conditions that health practitioners are unable to identify for most patients. A patient with prediabetes may not have any particular symptoms associated with diabetes, but the patient may still have risk factors that increase the risk of that particular patient developing diabetes. For example, age, weight, waist size, inactivity, family history, race, gestational diabetes, blood pressure, and sleep patterns are all attributes that can be measured to determine a risk factor of developing diabetes. If a doctor does not sit down with a patient with prediabetes and discuss the totality of these risk factors, or if the patient is not able to provide a comprehensive report on the spot with the pertinent facts, the doctor might not identify the true risk of that particular patient developing diabetes. However, it is likely that the patient has disclosed the totality of these risk factors throughout that patient's history of healthcare through various encounters.

Accordingly, there exists a need for a system and method for determining healthcare relationships to identify healthcare cost savings opportunities and improved patient health outcomes.

SUMMARY OF THE DISCLOSED EMBODIMENTS

In one aspect, a method for determining healthcare relationships includes ingesting, by a healthcare insight computing device, patient data of a patient received from one of a plurality of patient data providers; determining, by the healthcare insight computing device, one or more relationships between the ingested patient data and previously ingested patient data associated with the patient; correlating, by the healthcare insight computing device, the ingested data as a function of the determined relationships; enriching, by the healthcare insight computing device, the correlated patient data to form a new data element; and transmitting, by the healthcare insight computing device, the new data element to a raw data cluster.

In some embodiments, ingesting the patient data received from the patient data provider comprises staging the patient data in a data staging area. In other embodiments, determining the one or more relationships between the ingested patient data and the previously ingested patient data comprises determining the one or more relationships between the ingested patient data and the previously ingested patient data that has been received from another of the plurality of patient data providers.

In some embodiments, enriching the correlated patient data comprises supplementing the ingested patient data with referential data. In other embodiments, the method further includes extracting, by the healthcare insight computing device, at least a portion of the patient data from the raw data cluster in response to having received a request to generate a report associated with the patient data. Additionally or alternatively, in some embodiments, the method includes de-identifying, by the healthcare insight computing device, the extracted portion of the patient data; aggregating, by the healthcare insight computing device, the de-identified patient data as a function of the requested report; and presenting, by the healthcare insight computing device, a visual representation of the de-identified patient data as a function of the requested report and aggregated, de-identified patient data.

In some embodiments, the method additionally includes detecting, by the healthcare insight computing device, a previously identified relationship has been broken; and identifying, by the healthcare insight computing device, an alternative data path to form a new relationship with the patient data that was associated with the previously identified relationship.

BRIEF DESCRIPTION OF DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE DISCLOSED EMBODIMENTS

Figure 1:
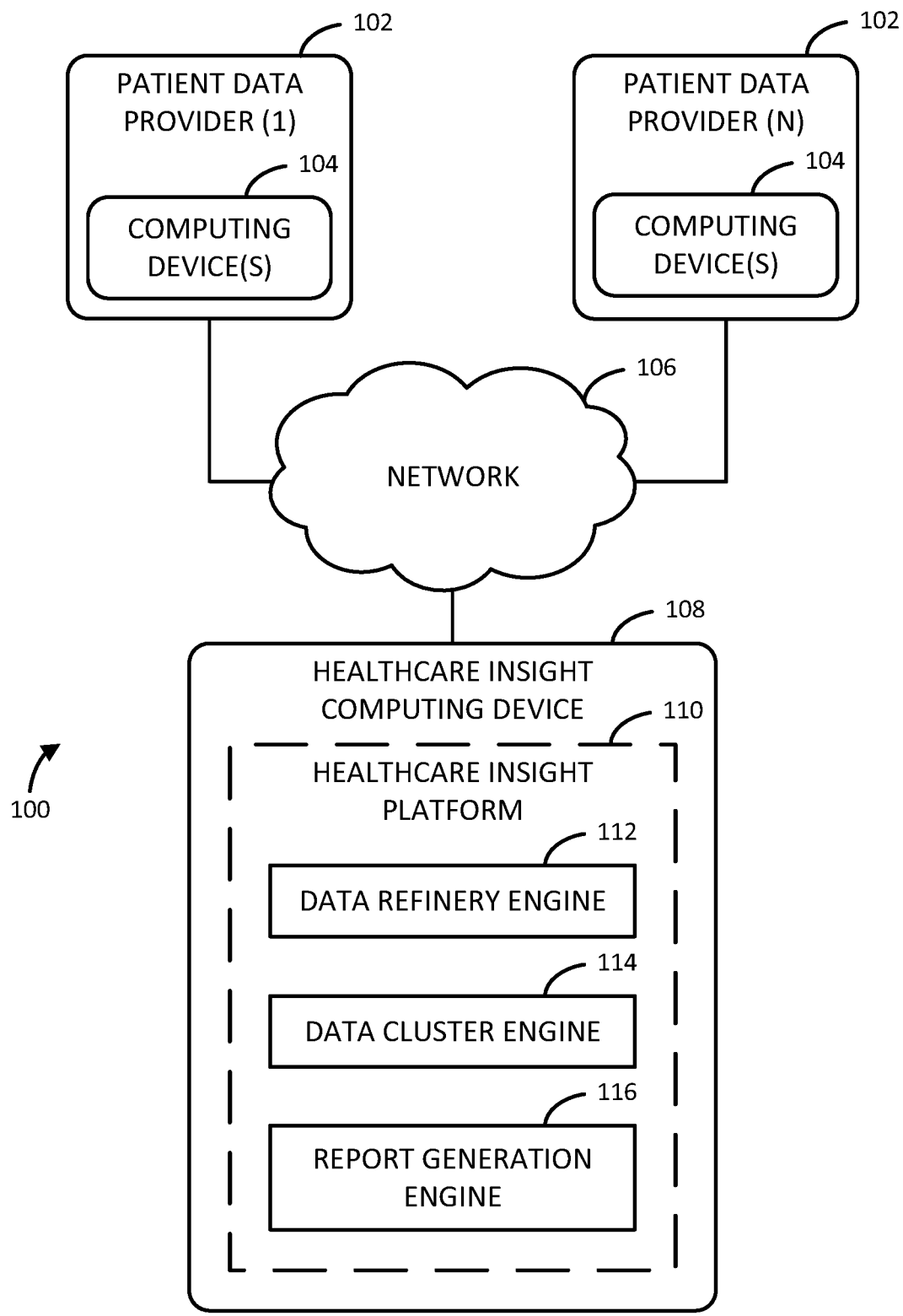
FIG. 1 is a schematic block diagram of an illustrative healthcare insight system for determining healthcare relationships that includes one or more patient data providers communicatively coupled, via a network, to a healthcare insight computing device.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This detailed description is presented in terms of programs, data structures, and/or procedures executed on a single computer or a network of computers. The software programs implemented by the system may be written in any programming language—interpreted, compiled, or otherwise. These languages may include, but are not limited to, PHP, ASP.net, HTML, HTML5, Ruby, Perl, Java, Python, C++, C#, JavaScript, and/or the Go programming language. It should be appreciated, of course, that one of skill in the art will appreciate that other languages may be used instead, or in combination with the foregoing and that web and/or mobile application frameworks may also be used, such as, for example, Ruby on Rails, Nodejs, Zend, Symfony, Revel, Django, Struts, Spring, Play, Jo, Twitter Bootstrap, and others. It should further be appreciated that the systems and methods disclosed herein may be delivered in a software-as-a-service (SaaS) model, made available over a computer network, such as, for example, the Internet. Further, the present disclosure may enable web services, application programming interfaces, and/or service-oriented architecture through one or more application programming interfaces (APIs) or other technologies.

FIG. 1 illustrates a healthcare insight system 100 for determining healthcare relationships. The healthcare insight system 100 includes one or more patient data providers 102 communicatively coupled to a healthcare insight computing device 108 via a network 106. The patient data providers 102 may include, but are not limited to, physicians, physician groups, pharmacies, hospitals, psychiatrists, clinics, laboratories, and/or any other entity or individual providing healthcare services and recording patient information in an electronic system.

In use, the healthcare insight computing device 108 receives various types of patient data from one or more of the patient data providers 102. The patient data may include any medical information related to a patient or healthcare provider (i.e., medical data), including, but not limited to provider information, physical characteristics of the patient (e.g., height, weight, race, etc.), medical history of the patient and/or family member (e.g., allergies, symptoms, diagnoses, treatments, lab results, outcomes, claims, etc.), and/or any other information related to the user that may be usable to perform the functions described herein, such as sleep patterns, activity levels, occupation, etc. Additionally, the patient data may include data referentially related to a patient (i.e., referential data), such as financial data, drug schedules, industry reference data, geographic data, etc. Accordingly, the patient data providers 102 may additionally include government agencies, financial institutions, industry organizations, census bureaus, etc.

It should be appreciated that the patient data may be pushed by one or more of the patient data providers 102 to the healthcare insight computing device 108 and/or pulled by the healthcare insight computing device 108 from one or more of the patient data providers 102 (e.g., from an electronic medical record database), depending on the embodiment. Due to the sensitive nature of the data being transmitted, it should be further appreciated that at least a portion of the patient data may be encrypted prior to transmission (e.g., to comply with government regulations, such as Health Insurance Portability and Accountability Act of 1996 (HIPAA)). The transmission of such patient data may be performed through web services, application programming interface (API), email, FTP, SFTP, or other data transfer processes. Additionally, data may be transmitted in various formats, such as a delimited text file (e.g., comma separated values (CSV) file, tab-separated values (TSV) file, etc.), Extensible Markup Language (XML), Health Level Seven International (HL7), or any other format.

Upon receiving the patient data, as further described in method 400 of FIG. 4 described below, the healthcare insight computing device 108 grooms the received data, analyzes the groomed data to determine various relationships and connections between the data (e.g., across patients, across data sets, etc.), Accordingly, unlike present technologies, the healthcare insight computing device 108 can detect relationships about a patient's entire healthcare experience. As such, large scale observations can be drawn about population trends as a result of being able to solve for an individual with confidence in those relationships at scale.

Additionally, the healthcare insight computing device 108 is configured to generate visualization report(s) usable to visualize the determined relationships/connections. For example, the visualization reports may be usable by healthcare providers to identify potential diagnoses of one or more patients, perform population health analysis, determine market conditions affecting pharmaceutical products, analyze the impact of programs on claims and testing behavior by healthcare providers, perform patient profiling, test innovations, etc.

As shown in the illustrative healthcare insight system 100 of FIG. 1, each of the patient data providers 102 includes one or more provider computing devices 104. Each of the provider computing devices 104 may be embodied as any type of computing device capable of performing the functions described herein, including providing a user interface for user interactions (e.g., the input of patient data), storing data, and/or transmitting the patient data from the patient data providers 102. Accordingly, the provider computing devices 104 may include, but are not limited to, a desktop computer, a mobile computing device, or any other type of "smart" or otherwise Internet-connected device. In such embodiments in which one or more of the provider computing devices 104 are embodied as a mobile computing device, it should be appreciated that those provider computing devices 104 may be embodied as any type of portable computing device that uses mobile-specific hardware and software components for operating, executing, and providing services and applications on a mobile architecture, such as smartphones, wearables (e.g., smartwatches, smart glasses, etc.), tablets, laptops, etc.

Figure 2:
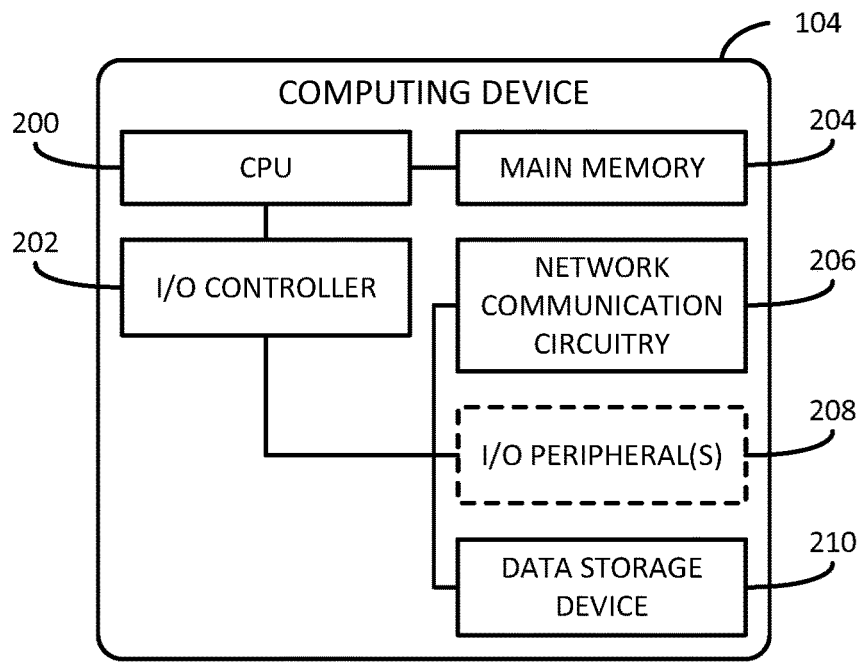
FIG. 2 is a schematic block diagram of an illustrative embodiment of one of the computing devices of the healthcare insight system of FIG. 1.

Referring now to FIG. 2, an illustrative embodiment of at least one of the provider computing devices 104 is shown. The illustrative provider computing device 104 includes a central processing unit (CPU) 200, an input/output (I/O) controller 202, a memory 204, a network communication circuitry 206, and a data storage device 210, as well as, in some embodiments, one or more I/O peripherals 208. It should be appreciated that alternative embodiments may include additional, fewer, and/or alternative components to those of the illustrative provider computing device 104, such as a graphics processing unit (GPU). It should be further appreciated that one or more of the illustrative components may be combined on a single system-on-a-chip (SoC) on a single integrated circuit (IC). Additionally, it should be appreciated that the type of components of the respective provider computing device 104 may be predicated upon the type and intended use of the respective provider computing device 104.

The CPU 200, or processor, may be embodied as any combination of hardware and circuitry capable of processing data. In some embodiments, the provider computing device 104 may include more than one CPU 200. Depending on the embodiment, the CPU 200 may include one processing core (not shown), such as in a single-core processor architecture, or multiple processing cores, such as in a multi-core processor architecture. Irrespective of the number of processing cores and CPUs 200, the CPU 200 is capable of reading and executing program instructions. In some embodiments, the CPU 200 may include cache memory (not shown) that may be integrated directly with the CPU 200 or placed on a separate chip with a separate interconnect to the CPU 200. It should be appreciated that, in some embodiments, pipeline logic may be used to perform software and/or hardware operations (e.g., network traffic processing operations), rather than commands issued to/from the CPU 200.

The I/O controller 202, or I/O interface, may be embodied as any type of computer hardware or combination of circuitry capable of interfacing between input/output devices and the provider computing device 104. Illustratively, the I/O controller 202 is configured to receive input/output requests from the CPU 200, and send control signals to the respective input/output devices, thereby managing the data flow to/from the provider computing device 104.

The memory 204 may be embodied as any type of computer hardware or combination of circuitry capable of holding data and instructions for processing. Such memory 204 may be referred to as main or primary memory. It should be appreciated that, in some embodiments, one or more components of the provider computing device 104 may have direct access to memory, such that certain data may be stored via direct memory access (DMA) independently of the CPU 200.

The network communication circuitry 206 may be embodied as any type of computer hardware or combination of circuitry capable of managing network interfacing communications (e.g., messages, datagrams, packets, etc.) via wireless and/or wired communication modes. Accordingly, in some embodiments, the network communication circuitry 206 may include a network interface controller (NIC) capable of being configured to connect the provider computing device 104 to a computer network (e.g., the network 106), as well as other devices, depending on the embodiment.

The one or more I/O peripherals 208 may be embodied as any auxiliary device configured to connect to and communicate with the provider computing device 104. For example, the I/O peripherals 208 may include, but are not limited to, a mouse, a keyboard, a monitor, a touchscreen, a printer, a scanner, a microphone, a speaker, etc. Accordingly, it should be appreciated that some I/O devices are capable of one function (i.e., input or output), or both functions (i.e., input and output).

In some embodiments, the I/O peripherals 208 may be connected to the provider computing device 104 via a cable (e.g., a ribbon cable, a wire, a universal serial bus (USB) cable, a high-definition multimedia interface (HDMI) cable, etc.) of the provider computing device 104. In such embodiments, the cable may be connected to a corresponding port (not shown) of the provider computing device 104 for which the communications made there between can be managed by the I/O controller 202. In alternative embodiments, the I/O peripherals 208 may be connected to the provider computing device 104 via a wireless mode of communication (e.g., Bluetooth®, Wi-Fi®, etc.) which can be managed by the network communication circuitry 206.

The data storage device 210 may be embodied as any type of computer hardware capable of the non-volatile storage of data (e.g., semiconductor storage media, magnetic storage media, optical storage media, etc.). Such data storage devices 210 are commonly referred to as auxiliary or secondary storage, and are typically used to store a large amount of data relative to the memory 204 described above.

Referring back to FIG. 1, the network 106 may be implemented as any type of wired and/or wireless network, including a local area network (LAN), a wide area network (WAN), a global network (the Internet), etc.. Accordingly, the network 106 may include one or more communicatively coupled network computing devices (not shown) for facilitating the flow and/or processing of network communication traffic via a series of wired and/or wireless interconnects. Such network computing devices may include, but are not limited, to one or more access points, routers, switches, servers, compute devices, storage devices, etc. It should be appreciated that, due to the sensitive nature of the patient data being transmitted, the communication channels used to transmit the patient data may be secured prior to transmission of the patient data.

The healthcare insight computing device 108 may be embodied as any type of compute and/or storage device capable of performing the functions described herein. For example, the healthcare insight computing device 108 may be embodied as, but is not limited to, one or more servers (e.g., stand-alone, rack-mounted, virtual, etc.), compute devices, cloud based compute services, storage devices, routers, switches, and/or combination of compute blades and data storage devices (e.g., of a storage area network (SAN)) in a cloud architected network or data center. As such, while the healthcare insight computing device 108 is illustrated as a single computing device, it should be appreciated that, in some embodiments, the healthcare insight computing device 108 may consist of more than one computing device (e.g., in a distributed computing architecture), each of which may be usable to perform at least a portion of the functions described herein.

It should be appreciated that the healthcare insight computing device 108 may contain like components to that of the illustrative provider computing device 104 of FIG. 2. Accordingly, such like components are not described herein to preserve clarity of the description. As described previously, the healthcare insight computing device 108 may include more than one computing device. As such, each computing device of the healthcare insight computing device 108 may include different components (i.e., hardware/software resources), the types of which may be predicated upon the type and intended use of each computing device. For example, one computing device of the healthcare insight computing device 108 may be configured as a database server with less compute capacity relative to the compute capacity of another of the computing devices of the healthcare insight computing device 108. Similarly, one computing device of the healthcare insight computing device 108 may be configured as an application server with more compute capacity relative to the compute capacity of another computing device of the healthcare insight computing device 108.

The illustrative healthcare insight computing device 108 includes a healthcare insight platform 110. The healthcare insight platform 110 may be embodied as any combination of hardware, firmware, software, or circuitry usable to perform the functions described herein. In some embodiments, the healthcare insight platform 110 may be embodied as any type of network-based software application (e.g., cloud application, network application, software-as-a-service (SaaS) application, etc.) configured to communicate with the patient data providers 102, or more particularly the provider computing devices 104 (e.g., in a client-server architecture). Accordingly, in such embodiments, one or more of the provider computing devices 104 may execute a client application, which may be embodied as a thin client (e.g., a web browser, an email client, etc.) or thick client, that is configured to communicate with the healthcare insight platform 110 over the network 106 to provide one or more of the services described herein to a user. It should be appreciated that, in some embodiments, the user as referred to herein may refer to a person (i.e., a human user) or the provider computing device 104 itself.

The illustrative healthcare insight platform 110 includes a data refinery engine 112, a data cluster engine 114, and a report generation engine 116. In some embodiments, the data refinery engine 112, the data cluster engine 114, and/or the report generation engine 116 may include one or more computer-readable medium (e.g., the memory 204, the data storage device 210, and/or any other media storage device) having instructions stored thereon and one or more processors (e.g., the CPU 200) coupled with the one or more computer-readable medium and configured to execute instructions to perform the functions described herein.

The data refinery engine 112, which may be embodied as any type of firmware, hardware, software, circuitry, or combination thereof, is configured to move the patient data from individual databases through a self-discovery mechanism that processes information by performing logical transformations to transform the patient data for optimization purposes (e.g., to remove duplicate copies of repeating patient data). To do so, the data refinery engine 112 may be configured to cleanse, massage, and refine data sets for aggregation, master data management, calculate confidence scores, and determine quality scores. The data refinery engine 112 is additionally configured to enrich the patient data sets (i.e., apply enrichment data) through additional data sources (e.g., the referential data) and referential replacements, as further disclosed herein.

In practice, different healthcare providers may input tests, medications, etc., into their respective systems (e.g. provider computing device 104) using different names/codes. Under such conditions, the data refinery engine 112 is configured to derive relationships such that the different names/codes can be correlated, normalized, etc. In an illustrative example, a first healthcare provider sees a patient for a particular condition. Data entry of the patient's data is entered into the various healthcare provider systems (e.g., electronic medical record management software, billing system, etc.) by the first healthcare provider.

However, in doing so, the patient's address was incorrectly entered. Despite this error, the patient is able to receive clinical service and receives a prescription. Subsequently, a second healthcare provider sees that same patient and, as a result of the patient's address being incorrectly entered by the first healthcare provider, the second healthcare provider is unaware that the patient has already been prescribed a medication for the ailment from the first healthcare provider. Accordingly, the patient may be prescribed the same medication by both healthcare providers, unbeknownst to either healthcare provider. Under such conditions in which the medication prescribed is a controlled substance, both healthcare providers have unwittingly provided a potential drug abuser/seller with a double dose of the controlled substance.

However, if such data is received by the data refinery engine 112 as described herein, the data refinery engine 112 can establish a relationship across the patient data received from the two healthcare providers using data received from the various data entry systems. For example, a first relationship can be established across the data sets received from the first healthcare provider, such that the incorrect address may be detected and the data normalized based on a correlation determined between not only the patient data received from the first healthcare provider, but also the patient data received from the second healthcare provider for that patient.

Additionally, a confidence level (i.e., confidence score, confidence rating, etc.,) of the detected relationship can also be increased, or decreased, as more patient data is correlated across the different sources of patient data sets associated with that patient. It should be appreciated that the degree to which the confidence level is increased or decreased may be predicated upon a weight associated with the type of data being compared. For example, the confidence level of an address of a patient will likely be different than the confidence level of a social security number of a patient.

The data cluster engine 114, which may be embodied as any type of firmware, hardware, software, circuitry, or combination thereof, is configured to house the resulting sets of the logical transformations performed by the data refinery engine 112. Unlike present technologies, in which a data analyzer may only be aware of a single route between tables and/or missing data might not allow a connection between tables to be established, the data cluster engine 114 is further configured to self-heal patient data pathways, thereby optimizing relationships between the patient data. To do so, the data cluster engine 114 is configured to find an optimal query and reroute the query to find an alternative connection path if any data is missing.

Additionally, the data cluster engine 114 is configured to calculate a score representative of the optimal possible paths. For example, in some embodiments, the data cluster engine 114 may be configured to find the shortest path in a weighted graph applied to database referential integrity (e.g., using the uniform-cost search (UCS) algorithm). In such embodiments, the "distance" cost between two tables of patient data is calculated based on the count of the rows in the union of two tables, a count of industry identifiers used, and a granularity match score.

The report generation engine 116, which may be embodied as any type of firmware, hardware, software, circuitry, or combination thereof, is configured to provide a visualization of the insight of the patient data relationships gathered through the data refinery engine 112 and the data cluster engine 114. To do so, the report generation engine 116 is configured to perform aggregation, rollups, metric calculations, algorithms, confidence scoring, and additional manipulation of the patient data as may be required for reporting, dashboards, and data mining.

It should be appreciated that while the individual relationships associated with one patient provide insights into that particular patient, those individual relationships can be aggregated to offer additional healthcare relationships and insights. To do so, a user can, via an interface to the reporting engine 116, request a visualization of a particular set of patient data, or a result of one or more relationships identified across multiple sets of patient data. For example, healthcare and government entities can analyze the relationships drawn by not only the standardization of clinical data elements, such as the testing, but also understand events across a true representation of the population because there is integrity in the number of patients that are accounted for. In turn, the education and/or prevention campaigns can be distributed across a number of healthcare providers to apprise the healthcare providers of trends. Additionally, targeted education efforts can be made to better services dynamics of an affected area, such as age, gender, etc.

Figure 3:
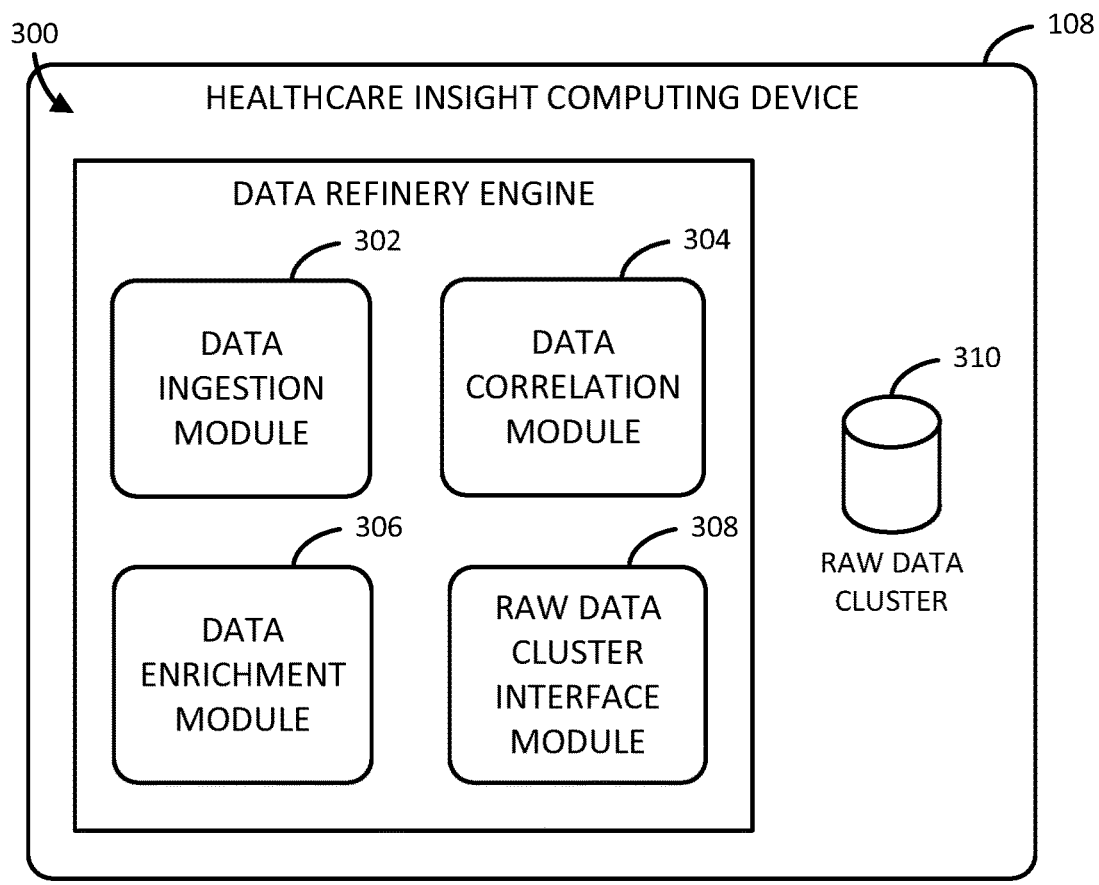
FIG. 3 is a schematic drawing of an illustrative embodiment of a healthcare insight platform of the data insight computing device of the healthcare insight system of FIG. 1.

Referring now to FIG. 3, an illustrative environment 300 of the healthcare insight platform 110 is shown. As described previously, the healthcare insight platform 110 may be embodied as any type of firmware, hardware, software, circuitry, or combination thereof capable of performing the functions described herein. The illustrative environment 300 includes a data ingestion module 302, a data correlation module 304, a data enrichment module 306, and a raw data cluster interface module 308. The illustrative environment 300 includes a raw data cluster 310. It should be appreciated that, in some embodiments, the raw data cluster 310 may be embodied as a single database, a distributed database, or an alternative database arrangement to that described herein. For example, in some embodiments, the raw data cluster 310 may be distributed across one or more healthcare insight computing devices 108.

The data ingestion module 302, which may be embodied as any type of firmware, hardware, software, circuitry, or combination thereof, is configured to ingest the data. In other words, the data ingestion module 302 is configured to obtain and import the patient data. Accordingly, in some embodiments, the data ingestion module 302 may be configured to stage the received patient data in an intermediate storage area (i.e., a staging area, a landing zone, etc.) in which the patient data can be stored temporarily. It should be appreciated that the data ingestion module 302 may be configured to import the data in real time (e.g., a stream) and/or in batches of data, depending on the type of data and/or the patient data provider 102 from which the patient data is being received. As described previously, the patient data may include medical data (e.g., provider information, physical characteristics, medical history of the patient and/or family member, etc.) and referential data (e.g., financial data, drug schedules, industry reference data, geographic data, etc.).

In some embodiments, access to the patient data obtained by the data ingestion module 302 may require authorization and/or that such data be encrypted while in storage and/or transit. Accordingly, in such embodiments, one or more authentication and/or encryption technologies known to those of skill in the art may be employed by the data ingestion module 302 to ensure the storage and access to the data complies with any legal and/or contractual requirements.

The data correlation module 304, which may be embodied as any type of firmware, hardware, software, circuitry, or combination thereof, is configured to correlate the patient data. To do so, for example, the data correlation module 304 may be configured to apply one or more transformation algorithms, normalization operations, refinement operations, etc., to the patient data to determine one or more relationships across the patient data. The data correlation module 304 is additionally configured to determine a confidence level for each data element of the patient data received, which may be weighted based on the type of patient data for which the confidence level corresponds. Accordingly, based on the confidence level, a degree of confidence can be established for each relationship.

The data enrichment module 306, which may be embodied as any type of firmware, hardware, software, circuitry, or combination thereof, is configured to enrich the correlated data to generate a new data element. To do so, for example, the data enrichment module 306 may be configured to add referential data to the correlated data. As described previously, the referential data may include any data that may not be explicitly associated with the patient that may be usable to further establish relationships between data sets, such as financial data, drug schedules, industry reference data, geographic data, etc.

The raw data cluster interface module 308, which may be embodied as any type of firmware, hardware, software, circuitry, or combination thereof, is configured to interface with the raw data cluster 310. For example, the raw data cluster interface module 308 is configured to transmit, or otherwise perform an operation to store data elements in the raw data cluster 310. Additionally, the raw data cluster interface module 308 is configured to extract data from the raw data cluster, such as may be requested by the reporting engine 116 when providing a visual representation of the data to a user.

Figure 4:
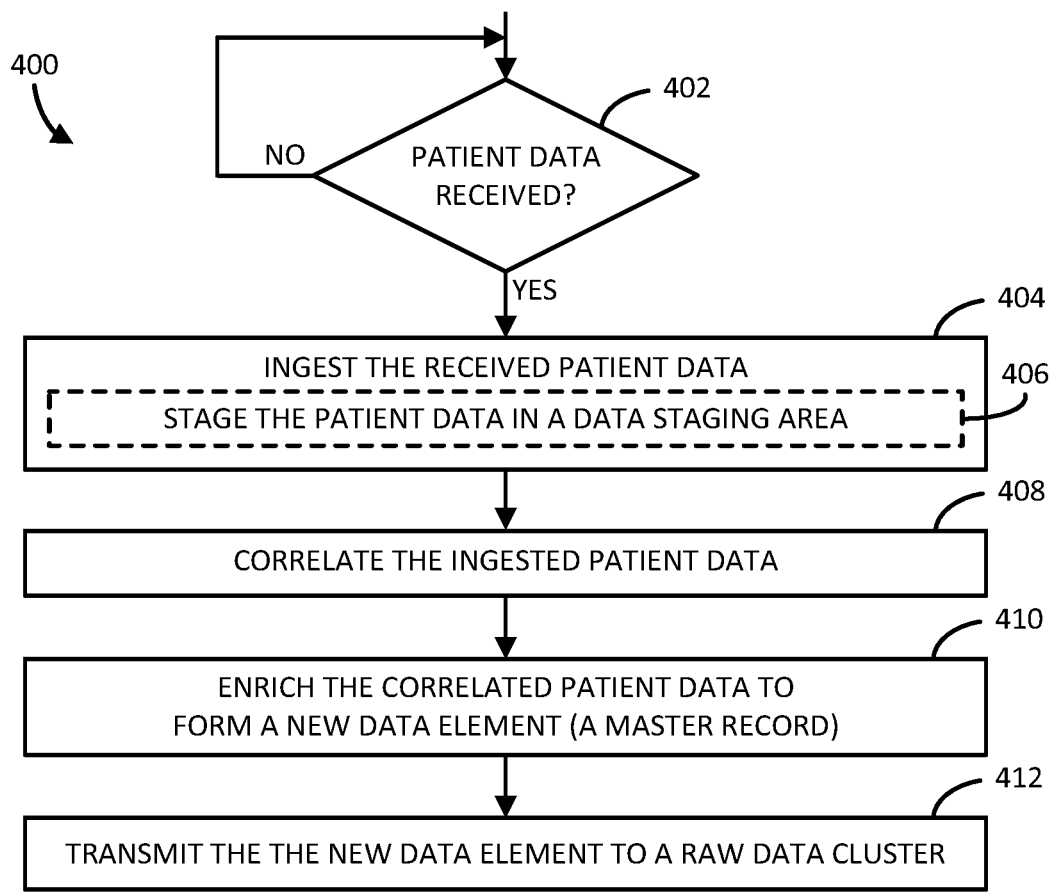
FIG. 4 is a schematic flow diagram of an illustrative method for determining healthcare relationships that may be performed by the data insight computing device of FIGS. 1 and 3.

Referring now to FIG. 4, an illustrative method 400 is provided for pre-identifying healthcare relationships that may be performed by the healthcare insight computing device 108, or more particularly by the data refinery engine 112 of the healthcare insight computing device 108. The method 400 begins in block 402, in which the data refinery engine 112 determines whether patient data has been received. As described previously, the patient data includes medical data, as well as referential data. Accordingly, the patient data may have been received by the data refinery engine 112 from a number of referential data sources or medical data sources. As described previously, the patient data may include medical data of the patient and/or referential data usable to establish relationships between the medical data and the referential data.

If patient data has been received, the method 400 advances to block 404, in which the data refinery engine 112 ingests the received patient data. To do so, in some embodiments, in block 406, the data refinery engine 112 stages the patient data in a staging area, or landing zone. In block 408, the data refinery engine 112 correlates the ingested patient data. To do so, the data refinery engine 112 may apply one or more transformation algorithms, normalization operations, refinement operations, etc., to the patient data to normalize the patient data and determine one or more relationships across the patient data. In block 410, the data refinery engine 112 enriches the correlated patient data to form a new data element (i.e., a master record). To do so, for example, the data refinery engine 112 may add referential data to the result of the patient data correlated in block 408. In block 412, the data refinery engine 112 transmits the new data element (i.e., a master record) to a raw data cluster (e.g., the raw data cluster 310 of FIG. 3).

Figure 5:
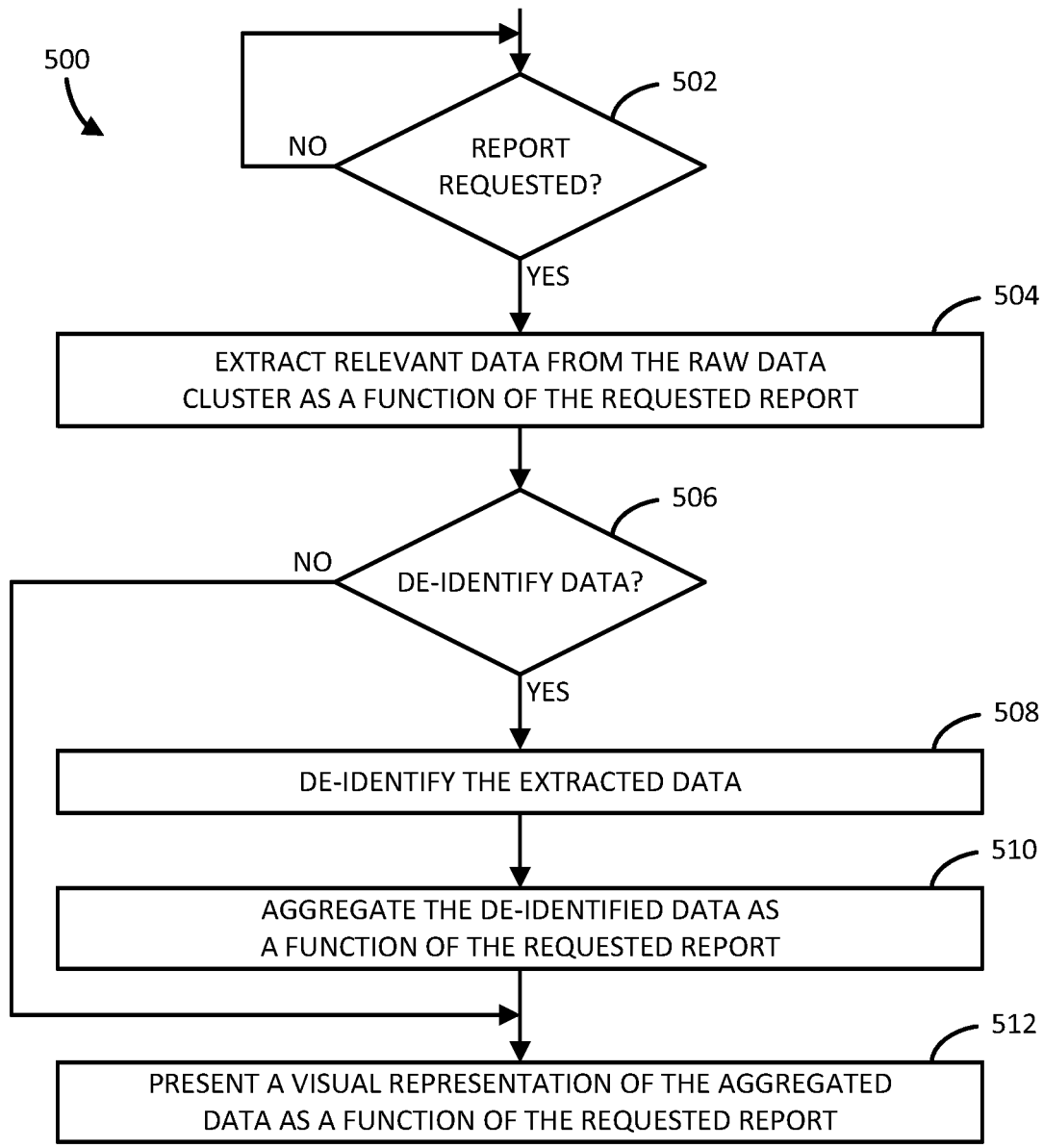
FIG. 5 is a schematic flow diagram of an illustrative method for presenting a visual representation of healthcare relationships that may be performed by the healthcare insight computing device of FIGS. 1 and 3.

Referring now to FIG. 5, an illustrative method 500 is provided for presenting a visual representation of healthcare relationships that may be performed by the healthcare insight computing device 108, or more particularly by the data cluster engine 114 and the report generation engine 116 of the healthcare insight computing device 108. The method 500 begins in block 502, in which the report generation engine 116 determines whether a report (i.e., a visual representation of data) has been requested. If so, the method 500 advances to block 504, in which the data cluster engine 114 extracts the relevant data from the raw data cluster as a function of the requested report. As described previously, a confidence level is associated with each relationship in the raw data cluster. In some embodiments, a confidence threshold may be set by a user requesting the report such that only the patient data associates with relationships meeting or exceeding the confidence threshold will be extracted.

As described previously, the raw data cluster includes patient data that can be classified as protected health information (PHI) and/or personally identifying information. Accordingly, in block 506, the data cluster engine 114 determines whether to de-identify the data (i.e., prevent a patient's identity from being connected with the patient information presented in the report). If not, the method 500 jumps to block 512, described below; otherwise, the method 500 advances to block 508. It should be appreciated that, in such embodiments in which the raw patient data is not de-identified, authorization may be required by the respective patients before the patient data can be provided in raw format.

In block 508, the data cluster engine 114 de-identifies the extracted data. In other words, the data cluster engine 114 removes any PII/PHI from the extracted data such that it cannot be used to identify patients associated with the retrieved data. For example, the data cluster engine 114 may be configured to mask or delete identifying information (e.g., names, social security numbers, etc.) and/or suppressing/generalizing quasi-identifying information (e.g., date of birth, address, phone number, etc.). In block 510, the data cluster engine 114 aggregates the de-identified data as a function of the requested report.

In block 512, the report generation engine 116 presents a visual representation of the aggregated data as a function of the requested report. The visual representation may include graphical and/or pictorial representations of the aggregated data and/or relationships, which may be presented as a web page featuring one or more objects, an application window featuring graphical user interface (GUI) elements, etc., depending on the embodiment. In some embodiments, the visualization may be interactive, allowing a user to interface with the visual representation such that the user can visually see the data at a more abstracted or granular level.

While the present disclosure has been illustrated and described in detail in the drawings and foregoing description, the same is to be considered as illustrative and not restrictive in character, it being understood that only certain embodiments have been shown and described, and that all changes and modifications that come within the spirit of the present disclosure are desired to be protected.

What is claimed is:

1. A computer-implemented method for determining healthcare relationships, the method comprising:
    ingesting patient data in real time, over the Internet, by a healthcare insight computing device, the healthcare insight computing device being addressable via the Internet, the patient data comprising medical information related to a patient in at least one of a plurality of formats;
    ingesting referential data, over the Internet, by the healthcare insight computing device, the referential data comprising data referentially related to the patient;
    applying, at a data refinery engine, at least one normalization algorithm on the patient data to create at least one correlation relationship;
    determining, at the data refinery engine, a confidence level for each data element of the patient data, the confidence level being representative of a likelihood that the data element has an appropriate correlation relationship;
    forming a master patient data record, at a data enrichment engine, the master patient data record comprising the patient data correlated with the referential data, and based at least in part on the at least one correlation relationship, the master patient data record being formed in a standard format for storage in a raw data cluster;
    transmitting, by the healthcare insight computing device, the master patient data record to the raw data cluster; and
    in response to receiving a request to generate a report associated with the patient data, generating, by the healthcare insight computing device, a visual representation of the requested report as a function of the master patient data record that comprises the patient data correlated with the referential data,
    wherein the requested report excludes any data element of the patient data having an associated confidence level that does not satisfy a confidence level threshold, and
    wherein any protected health information or personally identifying information in the master patient data is masked or deleted from the visual representation.

2. The method of claim 1, wherein the patient data is received from a plurality of patient data providers addressable via the Internet.

3. The method of claim 1, wherein the at least one normalization algorithm is selected from a group consisting of a transformation operation, a normalization operation, and a refinement operation.

4. The method of claim 2, wherein ingesting the patient data received from the plurality of patient data providers comprises staging the patient data in a data staging area.

5. The method of claim 2, wherein creating the at least one correlation relationship further comprises determining one or more relationships between the ingested patient data and a previously ingested patient data received from another of the plurality of patient data providers.

6. The method of claim 1, further comprising extracting, by the healthcare insight computing device, at least a portion of the patient data from the raw data cluster in response to having received the request to generate the report associated with the patient data.

7. A computer-implemented method for providing a healthcare request report, the method comprising:
retrieving, by a data cluster engine, a master patient data record from a raw data cluster over a raw data cluster interface, the master patient data record comprising patient data correlated with referential data, wherein the patient data comprises medical information related to a patient and the referential data comprises data referentially related to the patient, the patient data being ingested in at least one of a plurality of formats, wherein the master patient data record is generated based upon the patient data that has been ingested in real time and is formed in a standard format for storage in the raw data cluster;
determining, at a data refinery engine, a confidence level for each data element of the patient data, the confidence level being representative of a likelihood that the data element has an appropriate correlation relationship;
de-identifying, by a healthcare insight computing device, the master patient data record;
aggregating, by the healthcare insight computing device, the de-identified patient data as a function of the requested report; and
presenting, by the healthcare insight computing device, a visual representation of the de-identified patient data as a function of the requested report and aggregated, de-identified master patient data record,
wherein the requested report excludes any data element of the patient data having an associated confidence level that does not satisfy a confidence level threshold, and
wherein any protected health information or personally identifying information in the master patient data is masked or deleted from the visual representation based on the de-identified patient data.

8. The method of claim 7, further comprising:
detecting, by the healthcare insight computing device, a previously identified relationship has been broken; and
identifying, by the healthcare insight computer device, an alternative data path to form a new relationship with the master patient data record that was associated with the previously identified relationship.

9. A system for determining healthcare relationships, the system comprising:
a healthcare insight computing device addressable via the Internet, and configured to ingest patient data in real time, over the Internet, the patient data comprising medical information related to a patient in at least one of a plurality of formats;
the healthcare insight computing device further configured to ingest referential data, over the Internet, the referential data comprising data referentially related to the patient;
a data refinery engine configured to: (i) apply at least one normalization algorithm on the patient data to create at least one correlation relationship, and (ii) determine a confidence level for each data element of the patient data, the confidence level being representative of a likelihood that the data element has an appropriate correlation relationship;
a data enrichment engine configured to form a master patient data record, the data enrichment engine further configured to correlate the patient data with the referential data, and based at least in part on the at least one correlation relationship, the master patient data record being formed in a standard format for storage in a raw data cluster; and
wherein the healthcare insight computing device is further configured to transmit the master patient data record to the raw data cluster and to generate a visual representation of the requested report as a function of the master patient data record that comprises the patient data correlated with the referential data,
wherein the requested report excludes any data element of the patient data having an associated confidence level that does not satisfy a confidence level threshold, and
wherein any protected health information or personally identifying information in the master patient data is masked or deleted from the visual representation.

10. The system of claim 9, further comprising a plurality of patient data providers addressable via the Internet, and configured to transmit patient data therefrom.

11. The system of claim 10, wherein the healthcare insight computing device is further configured to stage the patient data in a data staging area.

12. A system for providing a healthcare request report, the system comprising:
a data cluster engine configured to retrieve a master patient data record from a raw data cluster over a raw data cluster interface, the master patient data record comprising patient data correlated with referential data, wherein the patient data comprises medical information related to a patient and the referential data comprises data referentially related to the patient, the patient data being ingested in at least one of a plurality of formats, wherein the master patient data record is generated based upon the patient data that has been ingested in real time and is formed in a standard format for storage in the raw data cluster;
a data refinery engine configured to determine a confidence level for each data element of the patient data, the confidence level being representative of a likelihood that the data element has an appropriate correlation relationship;
a healthcare insight computing device, configured to de-identify the master patient data record;
the healthcare insight computing device further configured to aggregate the de-identified patient data as a function of the requested report, and present a visual representation of the de-identified patient data as a function of the requested report and aggregated, de-identified master patient data record,
wherein the requested report excludes any data element of the patient data having an associated confidence level that does not satisfy a confidence level threshold, and
wherein any protected health information or personally identifying information in the master patient data is masked or deleted from the visual representation based on the de-identified patient data.

13. The system of claim 12, wherein the healthcare insight computing device is further configured to identify that relationship has been broken, and further identify an alternative data path to form a new relationship with the master patient data record that was associated with the previously identified relationship.

14. The method of claim 1, wherein the referential data includes financial data, drug schedules, industry reference data, and geographic data.

15. The method of claim 7, wherein the referential data includes financial data, drug schedules, industry reference data, and geographic data.

16. The system of claim 9, wherein the referential data includes financial data, drug schedules, industry reference data, and geographic data.

17. The system of claim 12, wherein the referential data includes financial data, drug schedules, industry reference data, and geographic data.

\* \* \* \* \*